United States Patent
Martin et al.

(10) Patent No.: US 6,616,936 B1
(45) Date of Patent: Sep. 9, 2003

(54) COMPOSITION COMPRISING AN OIL-IN-WATER EMULSION AND AN INORGANIC AGENT

(75) Inventors: Nadia Martin, Lyons (FR); Jean-Michel Mercier, Thiais (FR); Jean-Marc Ricca, Princeton, NJ (US)

(73) Assignee: Rhodia Chimie, Boulogne Billancourt Cedex (FR)

(*) Notice: Subject to any disclaimer, the term of this patent is extended or adjusted under 35 U.S.C. 154(b) by 0 days.

(21) Appl. No.: 09/890,964

(22) PCT Filed: Feb. 11, 2000

(86) PCT No.: PCT/FR00/00343

§ 371 (c)(1),
(2), (4) Date: Jan. 7, 2002

(87) PCT Pub. No.: WO00/49067

PCT Pub. Date: Aug. 24, 2000

(30) Foreign Application Priority Data

Feb. 18, 1999 (FR) .............................. 99 02010

(51) Int. Cl.$^7$ ............................ A61K 7/34; A61K 7/42; A61K 9/107; B01F 17/44
(52) U.S. Cl. ......................... 424/401; 424/59; 424/66; 516/58; 516/74
(58) Field of Search .................... 516/58, 74; 424/401, 424/59, 66

(56) References Cited

U.S. PATENT DOCUMENTS

| 4,254,104 | A | * | 3/1981 | Suzuki ................... 516/74 X |
| 4,797,273 | A | * | 1/1989 | Linn et al. ............... 516/58 X |
| 5,207,998 | A | * | 5/1993 | Robinson et al. ........ 514/944 X |
| 6,037,407 | A | * | 3/2000 | Derian et al. ............ 424/401 X |
| 6,048,519 | A | * | 4/2000 | Hiraishi et al. ......... 424/70.122 |
| 6,074,652 | A | * | 6/2000 | Ishiwatari et al. ........... 424/401 |
| 6,258,347 | B1 | * | 7/2001 | Sakuta et al. ........... 424/401 X |
| 6,261,543 | B1 | * | 7/2001 | Fletcher et al. ......... 424/401 X |

FOREIGN PATENT DOCUMENTS

| EP | 0 774 482 | 5/1997 | ............ C08J/3/03 |
| WO | WO 97 30130 | 8/1997 | ............ C07D/17/00 |

OTHER PUBLICATIONS

International Search Report.

* cited by examiner

Primary Examiner—Richard D. Lovering

(57) ABSTRACT

The invention concerns a composition comprising: 10 to 80 wt. % of at least an emulsion in water of a linear polydimethylsiloxane having a viscosity ranging between 1 and 5000 mPa.s at 25° C., the emulsion particles having a size of not more than 1 μm; and 1 to 50 wt. % of at least an inorganic agent; the complement for reaching 100 wt. % being an aqueous medium.

9 Claims, No Drawings

COMPOSITION COMPRISING AN OIL-IN-WATER EMULSION AND AN INORGANIC AGENT

This application is an application under 35 U.S.C. Section 371 of International Application Number PCT/FR00/00343 filed on Feb. 11, 2000.

The present invention relates to compositions comprising an oil-in-water emulsion and an inorganic agent, said compositions having improved stability and being capable of being used in cosmetics.

Many inorganic agents are used in the cosmetics industry to provide beneficial properties.

As an example, to overcome perspiration problems, antiperspirants are used that generally contain an astringent aluminum salt. To protect the skin from the effects of the sun, cosmetic compositions also contain mineral sunscreens the properties of which are often better than those of organic filters. Cosmetic compositions, in particular makeup, can also comprise mineral pigments.

In general, compositions comprising these inorganic agents are compositions based on a water-in-oil emulsion, the organic phase of this emulsion being a silicone compound. In the presence of an inorganic agent, such emulsions are highly unstable. In order to keep the emulsion and the composition stable, then, a particular type of silicone emulsifying agent has to be added, generally a polysiloxane, more particularly dimethylpolysiloxane, which contains polyoxyalkylenated (polyoxyethylenated and/or polyoxypropylenated)-dimethicone copolyol-chains.

Such compositions thus require the use of very particular, expensive stabilisation systems.

Compositions based on an oil-in-water emulsion are generally more stable. However, such emulsions are produced from non-ionic surfactant type emulsifying agents, and such compounds are not compatible with the inorganic agents introduced into the composition. Such a mixture results in unstable cosmetic compositions with a high tack, which are difficult to apply.

The present invention aims to produce stable compositions comprising:

an oil-in-water emulsion; and an inorganic agent.

The invention also aims to produce such compositions possessing low tack.

To this end, the invention concerns a composition comprising:

10% to 80% by weight of at least one emulsion in water of a straight chain polydimethylsiloxane with a viscosity in the range 1 to 5000 mPa.s at 25° C. the size of the particles in said emulsion being at most 1 μm;

1% to 50% by weight of at least one inorganic agent;

the complement to 100% by weight being an aqueous medium.

An essential feature of the composition of the invention is the nature of the organic phase of the oil-in-water emulsion.

This organic phase is a straight chain polydimethylsiloxane with a viscosity in the range 1 to 5000 mPa.s at 25° C. The viscosity of the polydimethylsiloxane is measured using a capillary viscometer using the method described in the Dow Corning Corporate Test Method CTM004, Jul. 20, 1970.

Preferably, a polydimethylsiloxane with a viscosity in the range 5 to 50 mPa.s. at 25° C. are used.

This type of straight chain polydimethylsiloxane is known as a dimethicone using the CTFA nomenclature. Such straight chain polydimethylsiloxanes are commercially available as the Viscasil® series from the General Electric Company, as the DC200® series from Dow Corning, and as the Mirasil DM® series from Rhodia Chimie.

Further, the size of the particles of the emulsion is at most 1 μm. The size of the particles of the emulsion is measured by laser diffraction granulometric analysis using a Horiba LA-910 granulometer.

Preferably, the size of the particles of the emulsion is in the range 0.2 to 0.8 μm.

This type of emulsion is prepared in a manner that is known to the skilled person.

A plurality of methods exist and have been described, in particular in the following references: "Understanding Emulsions (Randy Schueller and Perry Romanowski, Cosmetics & Toiletries Vol. 113, September 1998);" Formulating Cosmetic Emulsions (Dr Gillian M. Eccleston, Cosmetics & Toiletries Vol. 112, December 1997) and "Becher's Encyclopedia of Emulsion Technology" (P. Becher, Ed., M. Dekker 1983 and 1985).

More particularly, the amount of polydimethylsiloxane represents 20% to 80% by weight of the emulsion.

It should be noted that said emulsion may comprise at least one surfactant. Suitable surfactants will be described below.

Regarding the quantity of surfactant, this is more particularly in the range 0 to 10% by weight of the emulsion.

The aqueous phase of the emulsion is constituted by water, optionally combined with at least one monoalcohol or at least one polyalcohol, or mixtures thereof. Ethanol and propylene glycol are examples that can be cited.

Preferably, the emulsion represents 20% to 50% by weight of the composition, more preferably 20% to 30% by weight.

The inorganic agent in the composition of the invention can be selected from at least one of the following agents: inorganic pigments, mineral filters absorbing UVA and/or UVB radiation, and antiperspirants.

Inorganic pigments that can be cited include:

titanium dioxide (rutile or anatase), optionally surface treated, codified in the Color Index under reference number CI 77891;

black, red and brown iron oxides, codified under reference numbers CI 77499, CI 77492 and CI 77491;

manganese violet CI 77742;

ultramarine violet CI 77007;

ultramarine blue CI 77007;

chromium oxide CI 77288;

hydrated chromium oxide CI 77289;

ferric blue CI 77510.

Inorganic pigments that can be used include white pearl pigments such as micas coated with titanium oxide or bismuth oxide, or coloured pearl pigments such as mica-titanium coloured with iron oxides and mica-titanium coloured with an organic pigment.

The composition of the invention may comprise 5% to 50% by weight of at least one inorganic pigment, preferably 20% to 30%.

The compositions of the invention comprising inorganic pigments can be produced as face makeup compositions, foundations or lipsticks.

Mineral filters absorbing UVA and/or UVB radiation can be selected from metal oxides such as titanium dioxide (rutile or anatase, which may or may not be acicular), zinc oxide and iron oxide.

Preferably, titanium dioxide particles are used with a size in the range 20 to 200 nm surface coated with a mineral or organic coating. More particularly, aqueous dispersions of nanometric particles of titanium dioxide can be cited, with a size of less than 100 nm treated with a mineral based on silica and alumina. That type of dispersion has been described in International patents WO-A-97/30130 and WO-A-98/01392.

The composition of the invention can comprise 1% to 20% by weight of at least one mineral filter absorbing UVA and/or UVB radiation, preferably 2% to 8%.

Examples of compositions of the invention comprising mineral filters absorbing UVA and/or UVB radiation are sunscreens, day cream compositions or body lotions.

Antiperspirants act by reducing or even eliminating traces of perspiration on the skin surface. They have been described in "Woodruff's Ingredients and Formulary Handbook" (J. Woodruff—First Ed 1997 III p. 89).

The antiperspirant can be aluminum chloride, aluminum sulphate, aluminum hydrochloride, basic aluminum bromide, zirconium chloride, zirconium hydroxide, zirconium hydrochloride or complexes of the following types:

complexes of aluminum hydroxide, zirconium chloride and aluminum hydrochloride;

complexes of dihydroaluminium glycinate, zirconium chloride and/or hydrochloride and aluminum hydrochloride;

complexes of zirconium chloride and/or hydrochloride, aluminum hydrochloride and an amino acid such as glycine;

or mixtures of these products.

Preferred antiperspirant active principles are complexes of aluminum and zirconium hydrochlorides, for example: zirconium and aluminum trihydrochloride, zirconium and aluminum tetrahydrochloride and zirconium and aluminum pentahydrochloride, the names of which are defined in the CTFA nomenclature. These latter complexes can be combined with glycine.

The composition of the invention can comprise 5% to 40% by weight of at least one antiperspirant, preferably 15% to 25%.

In the case of an antiperspirant composition, it is preferably in the form of a roll-on applicator because of its low viscosity.

The viscosity of the composition of the invention is generally at most 100000 mPa.s at 25° C., preferably at most 5000 mPa.s, more preferably at most 1000 mPa.s.

The aqueous medium of the composition is at least constituted by water.

Preferably, however, the aqueous medium includes additives.

Possible additives that can be cited are anionic surfactants. These compounds are particularly advantageous, in particular in the case of low viscosity compositions, i.e., compositions with a viscosity of less than 5000 mPa.s.

The following anionic surfactants can be used:

alkylester sulphonates with formula R—CH(SO$_3$M)—COOR', where R represents a $C_8$–$C_{20}$ alkyl radical, preferably $C_{10}$–$C_{16}$, R' represents a $C_1$–$C_6$ alkyl radical, preferably $C_1$–$C_3$, and M represents an alkali cation (sodium, potassium, lithium), substituted or non substituted ammonium (methyl-, dimethyl-, trimethyl-, tetramethyl-ammonium, dimethylpiperidinium) or an alkanolamine derivative (a derivative of monoethanolarnine, diethanolamine, triethanolamine);

alkylsulphates with formula ROSO$_3$M, where R represents a $C_{10}$–$C_{24}$ alkyl or hydroxyalkyl radical, preferably $C_{12}$–$C_{20}$, M represents a hydrogen atom or a cation as defined above, and their ethoxylated (OE) and/or propoxylenated (OP) derivatives, preferably containing 1 to 20 OE motifs;

alkylamide sulphates with formula RCONHR'OSO$_2$M, where R represents a $C_2$–$C_{22}$ alkyl radical, preferably $C_6$–$C_{20}$, R' represents a $C_2$–$C_3$ alkyl radical, M represents a hydrogen atom or a cation with the same definition as defined above, and their ethoxylated (OE) and/or propoxylenated (OP) derivatives, preferably containing 1 to 20 OE motifs;

salts of saturated or unsaturated $C_8$–$C_{24}$ fatty acids preferably $C_{14}$–$C_{20}$, $C_9$–$C_{20}$ alkylbenzenesulphonates, and their ethoxylated (OE) and/or propoxylenated (OP) derivatives, preferably containing 1 to 20 OE motifs;

$C_9$–$C_{20}$ alkylbenzenesulphonates, primary or secondary $C_8$–$C_{22}$ alkylsulphonates, alkylglycerol sulphonates, sulphonated polycarboxylic acids described in British patent GB-A-1 082 179, paraffin sulphonates, N-acyl N-alkyllaurates, mono and dialkylphosphates, alkylisethionates, alkylsuccinamates, alkylsulphosuccinates, sulphosuccinate monoesters or diesters, N-acyl sarcosinates, alkylglucoside sulphates. polyethoxycarboxylates, the cation being an alkali metal (sodium, potassium, lithium), a substituted or non substituted ammonium residue (methyl-, dimethyl-, trimethyl-, tetramethyl-ammonium, dimethylpiperidinium) or a derivative of an alkanolamine (monoethanolamine, diethanolamine, triethanolamine).

Preferred surfactants are selected from: $C_6$–$C_{22}$ alkylethercarboxylates, $C_1$–$C_{23}$ alkylethersulphatecarboxylates, and alkylethersulphates comprising 1 to 23 OE and/or OP motifs per molecule.

In general, if such surfactants are employed, they are in amount of at most 5% of the composition weight. Preferably, this amount is in the range 0.01% to 5% by weight.

The composition of the invention can also contain at least one amphoteric surfactant, for example selected from alkylbetaines, ethyl aminopropyl betaines, alkylsulphobetains, alkyl amidopropyl hydroxysulphanes, alkyl glycinates and alkylcarboxyglycinates, in which the alkyl groups contain 8 to 18 carbon atoms.

The amount of amphoteric surfactant in the composition, when present, is at most 5% of said composition weight.

Preferably, the amount of amphoteric surfactant is in the range 0.01% to 5% by weight.

The composition of the invention can also comprise additives that are routinely introduced into cosmetic compositions, for example:

emollients such as:

alkylmonoglycerides, alkyldiglycerides, triglycerides such as oils extracted from plants and vegetables (palm oil, coprah oil, cottonseed oil, soya oil, sunflower seed oil, olive oil, grapeseed oil, sesame seed oil, peanut oil, castor oil, argan oil) or marine oils (fish oils), derivatives of such oils such as hydrogenated oils, lanolin effluents, mineral oils, or hydrocarbon oils such as paraffin oils, squalane, squalene, vaseline;

esters such as isopropyl myristate, isopropyl palmitate, butyl stearate, hexyl laurate, isononyl isononanoate, 2-ethylhexyl palmitate, 2-ethylhexyl laurate, 2-octyldecyl palmitate, 2-octyldodecyl myristate, 2-diethylhexyl succinate, diisostearyl malate, 2-octyldodecyl lactate, ethyl-2-hexyl cocoate, myristyl myristate, glycerine triisostearate;

silicone oils such as polymethylsiloxanes, polymethylphenylsiloxanes, polydiphenylsiloxanes, polyorganosiloxanes or polymethylsiloxanes modified by fatty acids, fatty alcohols, or fluorine-containing groups, silicone oils including α-ω hydroxylated polydimethylsiloxanes, α-ω trimethylsilylated polydimethylsiloxanes, aminated silicone derivatives such as amodithicone, silicone waxes or mixed silicone derivatives including different types of derivatives (such as mixed polyalkylmethylsiloxane-silicone copolyether copolymers), or perfluorinated and/or organofluorinated oils;

higher fatty acids;

myristic acid, palmitic acid, stearic acid, behenic acid, oleic acid, linoleic acid, linolenic acid, isostearic acid;

fragrances;

alcohols such as ethanol, glycerol, propylene glycol;

solubilising agents such as dipropyleneglycol monopropylether;

organic UV filters such as those mentioned in annex VII/I of European Directive No 76/78/EEC;

fillers such as hydrated magnesium silicates, aluminosilicates, modified or unmodified starch, silica, alumina, synthetic polymer powders (polyethylene, polyester, polyamide, polystyrene);

refreshing agents such as menthol, menthyl lactate and other menthol derivatives;

deodorants other than fragrances, which eliminate microbial flora, in particular malodorous flora, from the skin surface, for example 2,4,4'-trichloro-2'-hydroxydiphenyl ether (also known as DP300 or Triclosan®);

preservatives.

The composition of the invention can be prepared by diluting a prepared oil-in-water emulsion in water to the desired concentration and viscosity.

The inorganic agent is then added, and optionally the anionic surfactant and other additives.

It is possible to produce transparent compositions of the invention using a method that adjusts the refractive index; such methods have been described in "Woodruff's Ingredients & Formulary Handbook" (J. Woodruff—First Ed. 1997 III, p. 89).

This type of transparent formulation is of particular advantage in compositions comprising an antiperspirant.

The invention also concerns the use of this composition as a cosmetic composition. It is generally applied directly to the skin.

The following examples illustrate the invention without in any way limiting its scope.

EXAMPLES

Example 1

Antiperspirant Milk

An oil-in-water emulsion was prepared that was based on Mirasil DM20®, a dimethicone with a viscosity of 20 mPa.s, sold by Rhodia Chimie.

An anionic surfactant was used for emulsification: ethoxylated lauric alcohol sold by Rhodia Chimie, comprising 8 ethylene oxide units in an amount of 4% by weight with respect to the emulsion.

The emulsion obtained had a dimethicone content of 66% by weight and a particle size of 0.47 μm.

The dimethicone emulsion was mixed with water and laureth-8 carboxylate until a homogeneous mixture was obtained.

"Aluminum zirconium tetrachlorohydrex gly", an antiperspirant sold by REHEIS, was then added and the mixture was stirred until this agent had completely dissolved.

Finally, the fragrance and preservative were added.

The percentages by weight of the different components of the composition were as follows:

| | |
|---|---|
| Deionised water | 16.95 |
| Dimethicone emulsion | 60.7 |
| Laureth-8 carboxylate | 0.05 |
| Aluminium zirconium tetrachlorohydrex gly | 22 |
| Preservative and fragrance | 0.3 |

The composition obtained had a low viscosity, applied well and was completely tack-free.

No syneresis or sedimentation of the antiperspirant was observed on storage.

Example 2

Antiperspirant

An oil-in-water emulsion was prepared based on Mirasil DM20® sold by Rhodia Chimie.

An anionic emulsification agent, isotrideceth-7, was used for emulsification.

The emulsion had a dimethicone content of 66% by weight and a particle size of 0.47 μm.

The emulsion was stabilised by adding laureth-8 carboxylate in an amount of 0.05% by weight with respect to the emulsion.

The dimethicone emulsion was mixed with water until a homogeneous mixture was obtained.

"Aluminum zirconium tetrachlorohydrex gly" was then added and the mixture was stirred until this agent had completely dissolved.

Finally, the fragrance and preservative were added.

The percentages by weight of the different components of the composition were as follows:

| | |
|---|---|
| Deionised water | 32.75 |
| Dimethicone emulsion | 44.9 |
| Laureth-8-carboxylate | 0.05 |
| Aluminium zirconium tetrachlorohydrex gly | 22 |
| Preservative and fragrance | 0.3 |

The composition obtained was stable: no syneresis or sedimentation of the antiperspirant was observed on storage. It had a very slight tack when deposited on the skin.

Example 3

Transparent Antiperspirant

The dimethicone emulsion of Example 1 was mixed with water until a homogeneous mixture was obtained. "Aluminum zirconium tetrachlorohydrex gly" was then added and the mixture was stirred until this agent had completely dissolved. Finally, the fragrance and preservative were added.

The percentages by weight of the different components of the composition were as follows:

| | |
|---|---|
| Deionised water | 10.2 |
| Dimethicone emulsion | 66.0 |

| | |
|---|---|
| Aluminum zirconium tetrachlorohydrex gly | 23.5 |
| Preservative and fragrance | 0.3 |

The composition was translucid and readily deposited on the skin. It had no tack and remained stable on storage.

Example 4
Long Lasting Liquid Foundation

A dimethicone emulsion was prepared as described in Example 1, then two phases A and B were prepared by mixing their components.

The proportions of the different components with respect to the final composition were as follows:

| | |
|---|---|
| Phase A: | |
| Dimethicone emulsion | 20% by weight |
| Phenyltrimethicone | 2% by weight |
| Phase B: | |
| Propylene glycol | 0.3 |
| Mirasun TiW60 ®* | 3% by weight |
| Preservative | 0.3% by weight |
| Deionised water | 62.4% by weight |

*titanium dioxide based sunscreen, sold by Rhodia Chimie.

Phase B was added to phase A and the mixture was homogenised.

12% by weight with respect to the final composition of Nuancier Doré, a mixture of Covasop pigments in propylene glycol sold by Colorants Wackherr, was then introduced.

The foundation obtained was easy to apply to the skin, it was tack-free and it was long lasting.

Example 5
Foundation With UV Protection

A dimethicone emulsion was prepared as described in Example 1, then two phases A and B were prepared by mixing their components.

The proportions of the different components with respect to the final composition were as follows:

| | |
|---|---|
| Phase A: | |
| Dimethicone emulsion | 20% by weight |
| Diphenyldimethicone | 0.6% by weight |
| Cyclomethicone | 1.4% by weight |

| | |
|---|---|
| Phase B: | |
| Propylene glycol | 5% by weight |
| Mirasun TiW60 ® | 3 |
| Preservative | 0.3 |
| Xanthane gum | 0.2 |
| Deionised water | 57.75 |

Phase B was added to phase A and the mixture was homogenised.

11.75% by weight with respect to the final composition of Nuancier Doré, a mixture of Covasop pigments in propylene glycol sold by Colorants Wackherr, was then introduced.

The foundation obtained was easy to apply to the skin, it was tack-free and it was long lasting.

The sun protection factor (SPF), measured in vitro (Optometrics) as recommended by Colipa, was 6.3±0.8.

What is claimed is:

1. A composition comprising:
   10% to 80% by weight of at least one emulsion in water of a straight chain polydimethylsiloxane with a viscosity in the range from 1 to 5000 mPa.s at 25° C., said polydimethylsiloxane being in the form of particles having a size in the range from 0.2 to 0.8 μm;
   1% to 50% by weight of at least one inorganic agent; and
   an aqueous medium, being a complement to 100% by weight.

2. A composition according to claim 1, wherein the viscosity of the polydimethylsiloxane is in the range from 5 to 50 mPa.s. at 25° C.

3. A composition according to claim 1, wherein the composition is a cosmetic composition.

4. A composition according to claim 1, further comprising at least one anionic surfactant.

5. A composition according to claim 4, comprising at most 5% by weight of at least the anionic surfactant.

6. A composition according to claim 1, wherein the inorganic agent is selected from the group consisting of inorganic pigments, mineral filters absorbing UVA or UVB radiation, and antiperspirants.

7. A composition according to claim 6, comprising from 5% to 50% by weight of at least one inorganic pigment.

8. A composition according to claim 6, comprising from 1% to 20% by weight of at least one mineral filter absorbing UVA or-UVB radiation.

9. A composition according to claim 6, comprising from 5% to 40% by weight of at least one antiperspirant.

\* \* \* \* \*